United States Patent
Harmanli (10) Patent No.: US 8,302,608 B2
(45) Date of Patent: Nov. 6, 2012

(54) VAGINAL PESSARY

(75) Inventor: Oz Harmanli, Longmeadow, MA (US)

(73) Assignee: Oz Harmanli, Longmeadow, MA (US)

(*) Notice: Subject to any disclaimer, the term of this patent is extended or adjusted under 35 U.S.C. 154(b) by 570 days.

(21) Appl. No.: 12/482,043

(22) Filed: Jun. 10, 2009

(65) Prior Publication Data

US 2009/0283099 A1   Nov. 19, 2009

Related U.S. Application Data

(63) Continuation-in-part of application No. PCT/US2007/026016, filed on Dec. 19, 2007.

(60) Provisional application No. 60/871,272, filed on Dec. 21, 2006.

(51) Int. Cl.
*A61F 6/06* (2006.01)

(52) U.S. Cl. ............. 128/834; 128/885; 600/22; 600/37

(58) Field of Classification Search .................. 128/830, 128/832, 834, 839–840, 885, DIG. 25; 600/29–30
See application file for complete search history.

(56) References Cited

U.S. PATENT DOCUMENTS

| | | | |
|---|---|---|---|
| 328,553 A | 10/1885 | Warmoth | |
| 1,926,518 A | 9/1933 | Findley | |
| 2,234,495 A | 3/1941 | Lay | |
| 2,391,343 A | 12/1945 | Popper | |
| 2,540,325 A | 2/1951 | De Bray et al. | |
| 2,574,767 A | 11/1951 | Stubbs | |
| 4,286,593 A | 9/1981 | Place et al. | |
| 4,307,716 A | 12/1981 | Davis | |
| 4,821,741 A * | 4/1989 | Mohajer | 128/837 |
| 4,823,814 A | 4/1989 | Drogendijk et al. | |
| 4,920,986 A | 5/1990 | Biswas | |
| 5,224,494 A | 7/1993 | Enhorning | |
| 5,355,896 A | 10/1994 | Schulman | |
| 5,771,899 A * | 6/1998 | Martelly et al. | 128/830 |
| 5,894,842 A | 4/1999 | Rabin et al. | |
| 6,158,435 A | 12/2000 | Dorsey | |
| 6,189,535 B1 | 2/2001 | Enhorning | |
| 6,216,698 B1 | 4/2001 | Regula | |
| 6,418,930 B1 | 7/2002 | Fowler | |
| 6,458,072 B1 | 10/2002 | Zunker | |
| 6,460,542 B1 | 10/2002 | James | |
| 6,503,190 B1 | 1/2003 | Ulmsten et al. | |

(Continued)

FOREIGN PATENT DOCUMENTS

CH           354897         6/1961
(Continued)

*Primary Examiner* — Patricia Bianco
*Assistant Examiner* — Camtu Nguyen
(74) *Attorney, Agent, or Firm* — Holland & Bonzagni, P.C.; Mary R. Bonzagni, Esq.

(57) ABSTRACT

A compactable vaginal pessary for managing pelvic organ prolapse is provided. The compactable pessary easily expands once inside a patient's vagina, remaining firmly anchored in the vaginal cavity during movement, thereby effectively countering the effects of any prolapsing organ. In a first embodiment, the vaginal pessary employs an expandable and collapsible frame member, while in a second embodiment; the frame member is an open, substantially cone-shaped, collapsible frame member that is biased to an open position. In a third embodiment, the compactable vaginal pessary is a yieldably extensible, self-retracting pessary. The vaginal pessary of the present invention may be easily inserted and removed by a patient on a daily basis, or as needed, thereby facilitating good hygiene and thus reducing or eliminating common pessary related complications.

11 Claims, 6 Drawing Sheets

U.S. PATENT DOCUMENTS

| | | | |
|---|---|---|---|
| 6,645,137 B2 | 11/2003 | Ulmsten et al. | |
| 6,692,520 B1 | 2/2004 | Gambale et al. | |
| 6,808,485 B2 | 10/2004 | Zunker | |
| 7,036,511 B2 | 5/2006 | Nissenkorn | |
| 7,166,120 B2 * | 1/2007 | Kusleika | 606/191 |
| 2002/0083949 A1 | 7/2002 | James | |
| 2004/0084054 A1 | 5/2004 | Kaseki et al. | |
| 2004/0122285 A1 | 6/2004 | Zunker | |
| 2006/0122563 A1 | 6/2006 | Ziv | |
| 2008/0051740 A1 * | 2/2008 | Sokal et al. | 604/286 |

FOREIGN PATENT DOCUMENTS

| | | |
|---|---|---|
| DE | 271657 | 3/1914 |
| WO | WO2004103213 | 12/2004 |
| WO | WO2005087153 | 9/2005 |
| WO | WO2005087154 | 9/2005 |
| WO | WO 2006/097935 | 9/2006 |
| WO | WO2006097935 | 9/2006 |

* cited by examiner

VAGINAL PESSARY

RELATED APPLICATIONS

This application is a continuation-in-part application of, and claims priority to, International Application No. PCT/US2007/026016, filed Dec. 19, 2007, which in turn claims priority to U.S. Provisional Patent Application Ser. No. 60/871,272, filed Dec. 21, 2006, both of which are fully incorporated herein by reference.

TECHNICAL FIELD

The present invention generally relates to a vaginal pessary for managing pelvic organ prolapse, and more particularly relates to a vaginal pessary that may be easily inserted and removed by a patient on a daily basis, or as needed, thereby facilitating good hygiene and thus reducing or eliminating common pessary related complications.

BACKGROUND AND SUMMARY OF THE INVENTION

The pelvic floor is a group of muscles, ligaments and connective tissues that together support the pelvic organs. In women, the pelvic floor muscles form a supportive sheet to keep the bladder, the rectum and the uterus in place. These muscles are attached to the fixed framework of the pelvic bones.

Pelvic organ prolapse or POP occurs when the pelvic floor muscles are weakened thereby allowing one or more of these pelvic organs to push against the weakened wall of the vagina. POP, although not usually life threatening, affects urinary, sexual, and colorectal functions. For women with significant complaints, the management of POP currently consists of use of surgical reconstruction or vaginal pessaries.

Vaginal pessaries (i.e., plastic or silicone devices that are inserted into the vagina to help support the vaginal walls and pelvic organs) are used for POP reduction in women who prefer conservative treatment. Periodic removal of these devices, however, is necessary to maintain good hygiene and to reduce or eliminate complications caused at least in part by the prolonged presence of these devices in the vagina, such complications including irritation, erosion, bleeding and malodorous discharge. Ideally, pessaries should be removed on a daily basis.

Unfortunately, a majority of prior art pessaries must be manually squeezed or bent in order to be inserted or removed from the body, thus making self-insertion almost impossible, especially for older women. In fact, only about 5% of patients are able to remove and reinsert their own pessaries, with the majority of patients forced to rely on lifelong regular office visits every two to three months, with each visit including removal, cleaning and reinsertion of the pessary along with a thorough inspection of the vagina. Even in the most experienced hands, removal is very difficult, and sometimes inhumane by today's standards. Most of the time, patients leave the office with small but painful abrasions of the vaginal introitus. This stressful experience is the main reason for pessary discontinuation, and consideration of a reconstructive surgical procedure.

In view of the above, it is a general object of the present invention to provide a vaginal pessary that avoids the drawbacks associated with these prior art pessaries.

It is a more particular object to provide a vaginal pessary that: (a) is easy for a patient to insert and remove from the vaginal cavity; (b) remains firmly anchored in the vaginal cavity during movement, such as coughing, sneezing, laughing, or during exercise; and (c) more effectively controls POP, whether in the form of cystoceles (herniation of the urinary bladder through the wall of the vagina), rectoceles (herniation of the rectum into the vagina), uterine prolapse, and/or vaginal prolapse.

It is another more particular object to provide different embodiments of the inventive vaginal pessary, all of which satisfy the objects identified above.

The present invention therefore provides a compactable vaginal pessary that easily expands once inside a patient's vagina, that can be removed, cleaned and reinserted daily, or as needed, by the patient.

In a first embodiment, the vaginal pessary of the present invention basically comprises: (a) an expandable and collapsible frame member; (b) optionally, a protective cover or sleeve for partially encasing the frame member, and (c) means for (i) expanding the frame member, (ii) retaining the frame member in an expanded configuration, and (iii) collapsing the expanded frame member.

When the frame member is in a collapsed state, the pessary may be easily inserted into the vagina. Once in place, the frame member is expanded, and prior to removal of the pessary, the frame member is returned to a collapsed state.

In a second embodiment, the inventive vaginal pessary basically comprises: (a) an open, substantially cone-shaped, collapsible frame member, the frame member being biased to an open position and comprising a central hub, and a plurality of flexible and resilient spokes emanating from the central hub; (b) a flexible and resilient sheet-like material connecting the spokes of the frame member; and (c) withdrawal means attached to the central hub of the frame member.

The frame member is collapsed prior to insertion of the pessary into the vagina, and once in place in the vagina, the frame member is allowed to adopt an open, substantially conical configuration. Prior to removal of the pessary, the frame member is returned to a collapsed configuration.

In a third embodiment, the inventive vaginal pessary is a yieldably extensible, self-retracting pessary that basically comprises: (a) an elongate cylindrical body having a distal end and a proximal end; (b) optionally, a protective cover or sleeve for encasing the elongate cylindrical body: and (c) withdrawal means attached to the proximal end of the elongate cylindrical body. Prior to insertion into the vagina, the pessary is straightened and, upon proper placement in the vagina, is allowed to adopt a coiled configuration.

Other features and advantages of the invention will be apparent to one of ordinary skill from the following detailed description and accompanying drawings. Unless otherwise defined, all technical and scientific terms used herein have the same meaning as commonly understood by one of ordinary skill in the art to which this invention belongs. All publications, patent applications, patents and other references mentioned herein are incorporated by reference in their entirety. In case of conflict, the present specification, including definitions, will control. In addition, the materials, methods, and examples are illustrative only and not intended to be limiting.

BRIEF DESCRIPTION OF THE DRAWINGS

Particular features of the disclosed invention are illustrated by reference to the accompanying drawings in which.

BEST MODE FOR CARRYING OUT THE INVENTION

As noted above, the vaginal pessary of the present invention allows a patient to insert and remove the pessary herself on a daily basis, or as needed, thereby facilitating good hygiene and thus reducing or eliminating common pessary related complications (e.g., irritation, bleeding, malodorous discharge, erosion). The inventive pessary remains firmly anchored in the vaginal cavity during movement, and effectively counters the effects of any prolapsing organ.

In a first embodiment, the vaginal pessary of the present invention is capable of expanding and collapsing and basically comprises:

(a) an expandable and collapsible frame member, wherein the frame member comprises:
  (i) coaxial outer and inner elongated cylindrical members, the outer elongated cylindrical member being slidably disposed on the inner elongated cylindrical member and having opposing upper and lower ends, with the upper end terminating in, or fixably attached to, an upper bulb-shaped hub, the inner elongated cylindrical member having opposing upper and lower ends, with the lower end terminating in, or fixably attached to, a lower bulb-shaped hub; and
  (ii) a plurality of flexible and resilient spokes surrounding the outer and inner elongated cylindrical members, and fixably attached to both the upper and lower hubs;

(b) optionally, a protective cover or sleeve for partially encasing the frame member; and (c) means for (i) expanding the frame member, (ii) retaining the frame member in an expanded configuration, and (iii) collapsing the expanded frame member.

The vaginal pessary of this first embodiment has, in its expanded state, a maximum outer diameter or major axis that exceeds the midsagittal vaginal diameter, and is sufficiently stiff to resist deforming stresses exerted by the vaginal wall muscles.

Figure 1:
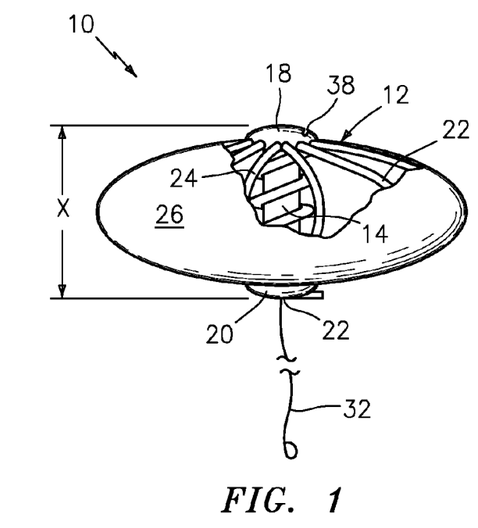
FIG. 1 is a partial cut-away side view of the first embodiment of the vaginal pessary of the present invention showing the frame member in its expanded configuration.
Figure 2:
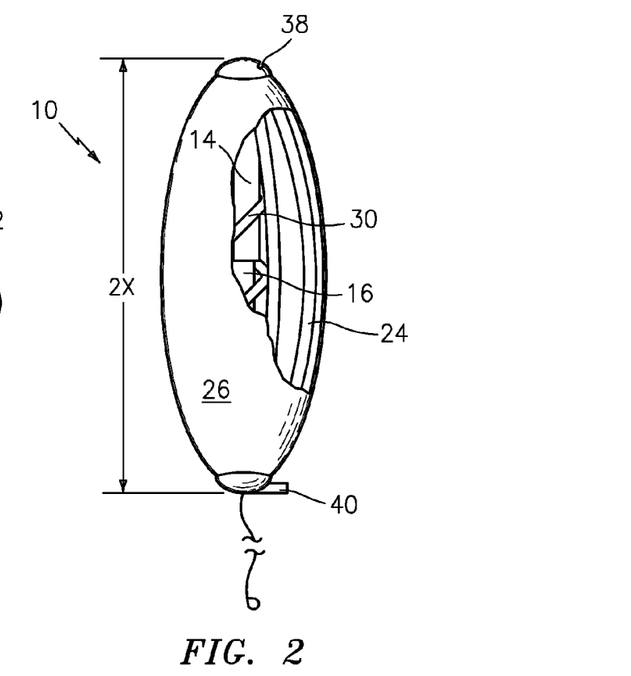
FIG. 2 is a partial cut-away side view of the vaginal pessary of FIG. 1 showing the frame member in its collapsed state.
Figure 3:
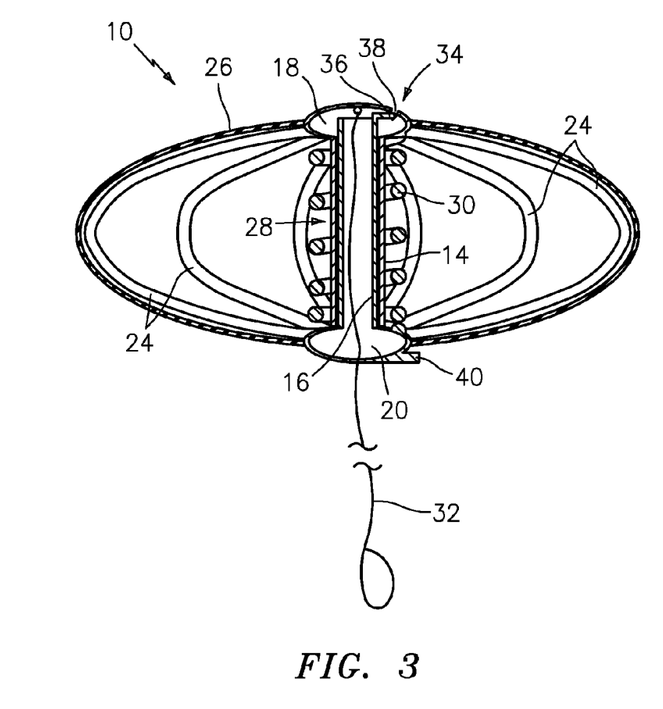
FIG. 3 is an enlarged cross-sectional side view of the vaginal pessary shown in FIG. 1.

While the inventive vaginal pessary may adopt any suitable shape, in a preferred embodiment, as best shown in FIGS. 1 to 3, the inventive vaginal pessary adopts an elongated prolate ellipsoid-like shape when in a collapsed state (see FIG. 2), and an oblate ellipsoid-like shape when in an expanded state (see FIGS. 1 and 3).

The inventive vaginal pessary in its collapsed state is sized or dimensioned to facilitate insertion into and withdrawal from the vagina. In a preferred embodiment, the collapsed vaginal pessary has a minor axis length or width ranging from about 2.5 to about 4.5 centimeters (cm) and a major axis length or height ranging from about 5.0 to about 9.0 cm.

The inventive vaginal pessary in its expanded state is sized or dimensioned to suit the individual requirements of the patient. Where each patient has different vaginal dimensions and different requirements in terms of the pressure that the inventive vaginal pessary must exert in order to achieve its objectives, it is intended that the vaginal pessary of this first embodiment be available in a number of sizes, with minor axis lengths or heights in the expanded state ranging from about 2.5 to about 4.5 cm and major axis lengths or widths ranging from about 5.0 to about 9.0 cm.

As alluded to above, the expandable and collapsible frame member is sufficiently rigid to retain its shape against the pressure exerted by the vaginal walls, while having sufficient flexibility and resiliency to be collapsible for introduction into and removal from the vagina. In a preferred embodiment, the coaxial outer and inner elongated cylindrical members (including the upper and lower hubs) are formed from a rigid material such as stainless steel, while the flexible and resilient spokes are formed from shape memory alloys or other material exhibiting similar super-elastic characteristics.

In order to facilitate uniform spacing between the spokes when the inventive pessary is in its expanded state, the frame member may further comprise a flexible and s resilient band affixed mid-way along an outer or inner surface of each spoke.

A protective cover or sleeve may be used to partially encase the frame member, covering the spokes while leaving the upper and lower hubs exposed. The protective cover or sleeve may be made of a flexible, resilient and impermeable biocompatible material (i.e., materials that do not incite toxic reactions). Suitable materials include polyethylene, polyvinyl chloride, urethane, silicone rubber, and the like.

The expanding/retaining/collapsing means of the vaginal pessary of this first embodiment is not limited and may be any suitable mechanical and/or electronic means.

Referring now to FIGS. 1 to 3 in detail, reference numeral 10 has been used to generally designate a preferred first embodiment of the inventive vaginal pessary in which the expanding/retaining/collapsing means is mechanical in nature. In this preferred embodiment, vaginal pessary 10 generally comprises:

(a) an expandable and collapsible frame member 12, which comprises:
  (i) coaxial outer and inner elongated cylindrical members 14, 16, the outer elongated cylindrical member 14 having opposing upper and lower ends, with the upper end terminating in, or fixably attached to, an upper bulb-shaped hub 18, the inner elongated cylindrical member 16 having opposing upper and lower ends, with the lower end terminating in, or fixably attached to, a lower bulb-shaped hub 20 having a small central opening 22; and
  (ii) a plurality of flexible and resilient spokes 24 surrounding the outer and inner elongated cylindrical members 14, 16, and fixably attached to both the upper and lower hubs 18, 20;
(b) a protective cover or sleeve 26 for partially encasing the frame member 12; and
(c) expanding/retaining/collapsing means 28, which comprises:
  (i) a helical spring or spring-like member 30 surrounding the coaxial outer and inner elongated cylindrical members 14, 16;
  (ii) a cord, string or tape 32 having a length ranging from about 15 cm to about 30 cm, attached to an inner surface of upper hub 18, which extends through cylindrical members 14, 16 and out through opening 22 of lower hub 20;
  (iii) locking/releasing mechanism 34 comprising a projection 36 emanating from the upper end of the inner elongated cylindrical member 16, an opening 38 in upper hub 18 that is shaped to receive projection 36, and a projection 40 emanating from an outer surface of lower hub 20.

Figure 4:
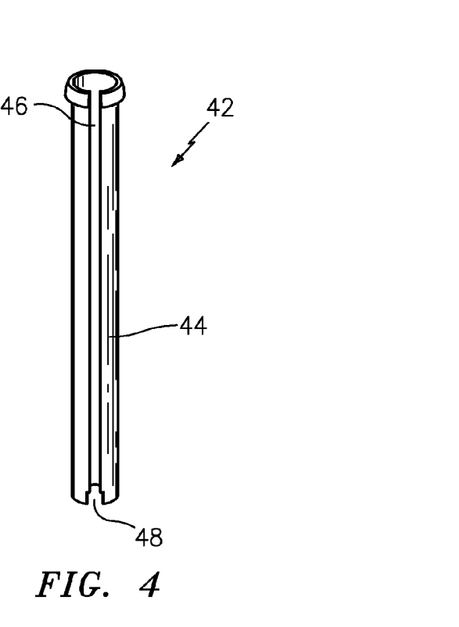
FIG. 4 is a side view of a device for inserting and removing the vaginal pessary of FIG. 1 into and out of the vagina.

Device 42, which is shown in FIG. 4, is used in conjunction with pessary 10 and comprises an elongate cylindrical body 44 having a slot-shaped opening 46 that extends along the longitudinal axis of body 44 and terminates in an opening 48 shaped to receive projection 40 of lower hub 20. Device 42 is used by a patient to insert pessary 10, while in a collapsed configuration, into the vagina and when properly placed within the vagina, to expand the pessary 10 and to lock the pessary 10 in its expanded configuration. Device 42 is also used by the patient to collapse the pessary 10 prior to removal from the vagina.

More specifically, prior to insertion into the vagina, a patient would line up the opening 48 on device 42 with the projection 40 on lower hub 20 of pessary 10, while guiding cord, string or tape 32 through the slot-shaped opening 46 of device 42. The patient would then position the pessary 10 at the mouth of the vagina, apply an upward force on device 42 to push pessary 10 into the vagina, and once properly positioned, expand pessary 10 by simultaneously applying upward pressure on device 42, while pulling down on the cord, string or tape 32. Once fully expanded, the patient would rotate device 42 and concomitantly inner elongate cylindrical member 16 until projection 36 is fully engaged in opening 38 of upper hub 18, thereby locking pessary 10 in its expanded configuration.

When the patient is ready to remove vaginal pessary 10, she would insert the device 42 into the vagina, line up the opening 48 on device 42 with the projection 40 on lower hub 20 of pessary 10, and rotate device 42 and concomitantly inner elongate cylindrical member 16 until projection 36 fully disengages from opening 38 of upper hub 18, thereby collapsing pessary 10. Collapsed pessary 10 and device 42 would then be easily and comfortably removed from the vagina by the patient applying a gentle downward force on cord, string or tape 32. The pessary 10 and device 42 would then be cleaned and stored until they were needed again by the patient.

Figure 5:
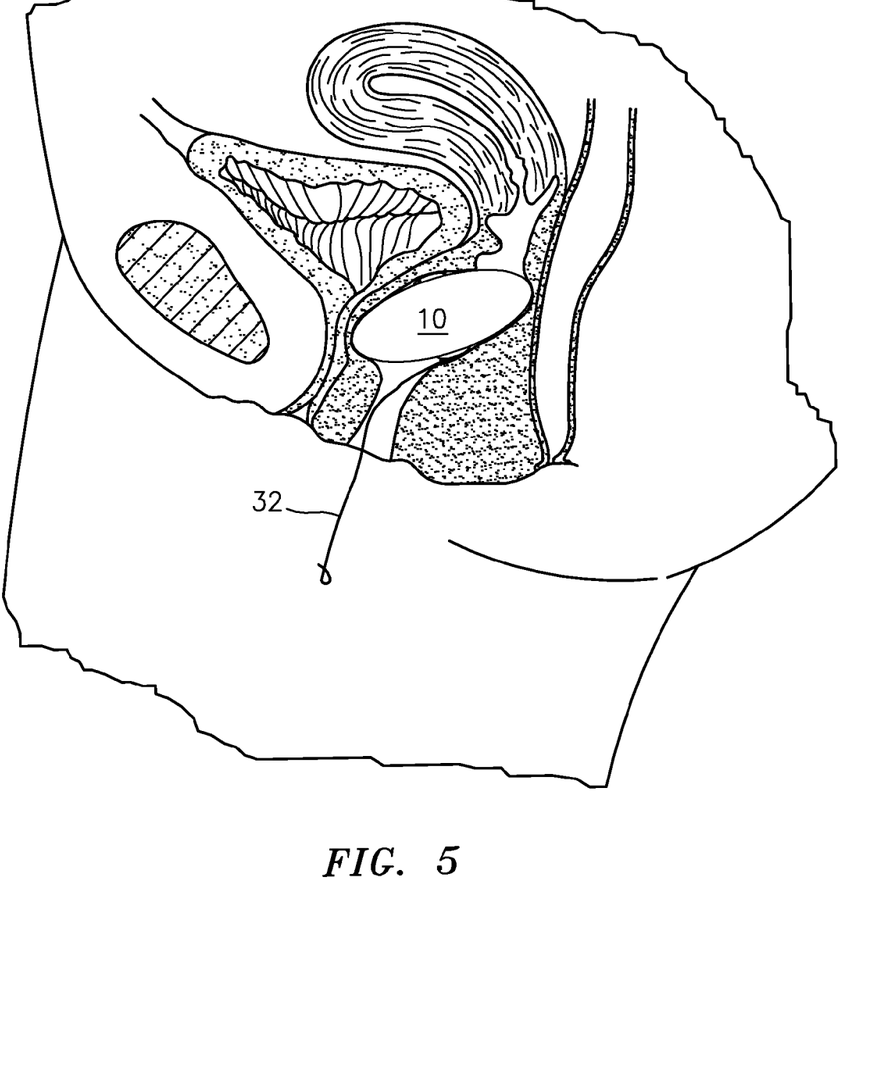
FIG. 5 is a diagrammatic cross-sectional view of the female urogenital system showing the vaginal pessary of FIG. 1 in place within the vagina.

As best shown in FIG. 5, which is a diagrammatic cross-sectional view of the female urogenital system showing expanded vaginal pessary 10 in place within the vagina, expanded vaginal pessary 10 fully and effectively counters the effects of any prolapsing organ, such as the urinary bladder, uterus or rectum, into the vagina or vaginal vault.

Referring now to FIGS. 6 to 10, in detail, reference number 50 has been used to generally designate two variations of a second embodiment of the vaginal pessary of the present invention. In this second embodiment, vaginal pessary 50 has an inverted, umbrella-like appearance and basically comprises:
(a) an open, substantially cone-shaped, collapsible frame member 52, the frame member 52 being biased to an open position and comprising an inverted substantially dome-shaped central hub 54, and a plurality of flexible and resilient spokes 56 emanating from the central hub 54, with each spoke 56 having a blunt, rounded or shaped proximal end 58;
(b) a flexible and resilient sheet-like material 60 connecting the spokes 56 of the frame member 52; and
(c) withdrawal means 62 attached to the central hub 54 of frame member 52.

Figure 6:
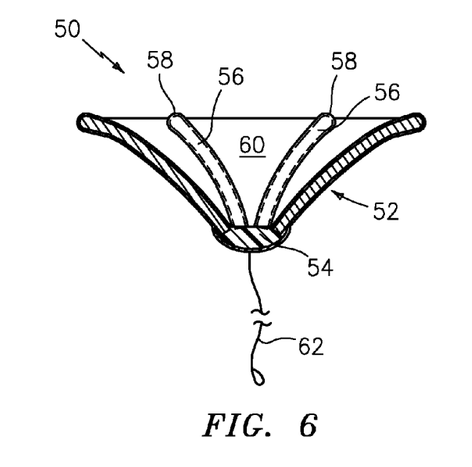
FIG. 6 is a cross-sectional side view of a variation of the second embodiment of the vaginal pessary of the present invention showing the frame member in its normally open state.
Figure 7:
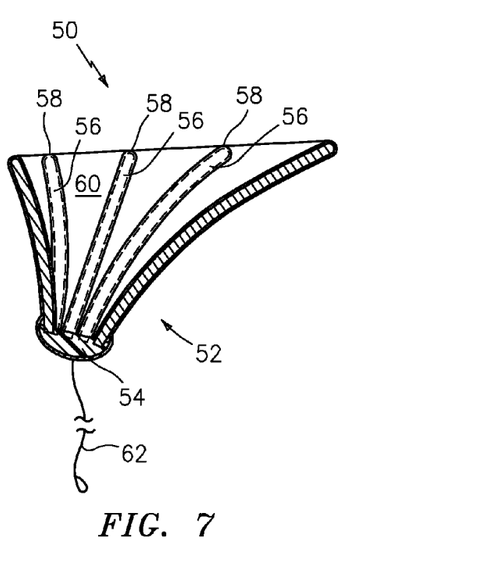
FIG. 7 is a cross-sectional side view of another variation of the second embodiment of the vaginal pessary of the present invention also showing the frame member in its normally open state.

As best shown in FIGS. 6 and 7, collapsible frame member 52 may be symmetric or asymmetric in design. For example, the transverse cross-sectional shape of collapsible frame member 52, as defined by the opening formed by the proximal ends 58 of spokes 56, may be circular (see FIG. 6) or oval, semi-oval, elliptical (see FIG. 7), or semi-elliptical. Where the asymmetrical design shown in FIG. 7 more closely conforms to vaginal anatomy, this variation may prove to be more comfortable to patients.

Similar to that noted above with respect to the first embodiment, vaginal pessary 50 in its normally open state has a maximum outer diameter that exceeds the midsagittal vaginal diameter and is sufficiently stiff to resist deforming stresses exerted by the vaginal wall muscles while in place in the vagina.

Figure 9:
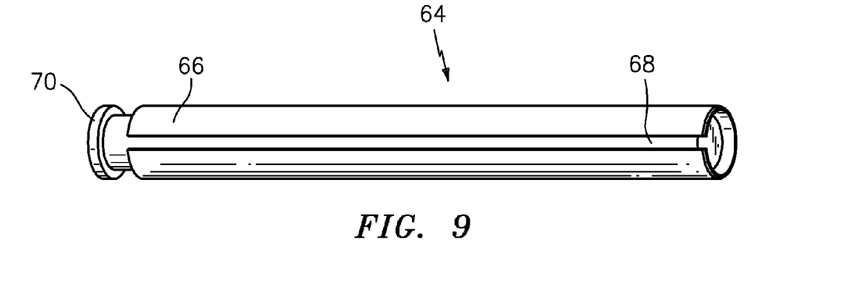
FIG. 9 is a side view of a device for inserting and removing the vaginal pessary of FIGS. 6 and 7 into and out of the vagina.

Vaginal pessary 50, in its collapsed state, fits inside any appropriate insertion/withdrawal tool or device, such as that shown in FIG. 9. Preferably, vaginal pessary 50 has a maximum outer diameter or width in its collapsed state that does not exceed 4.5 cm.

Vaginal pessary 50, in its normally open state, is sized or dimensioned to suit the individual requirements of the patient. It is intended that the vaginal pessary of this second embodiment be available in a number of sizes, with maximum outer diameters ranging from about 5.0 to about 9.0 cm, and maximum heights ranging from about 2.5 to about 4.5 cm.

As alluded to above, the frame member 52 of vaginal pessary 50 is sufficiently rigid to retain its open, substantially conical shape against the pressure exerted by the vaginal walls, while having sufficient flexibility to be collapsible for introduction into and removal from the vagina. In a preferred embodiment, the inverted substantially dome-shaped central hub 54 is formed from a flexible, biocompatible material selected from the group of polyethylene, polyvinyl chloride, urethane, silicone rubber, and the like, while the spokes 56, which radiate from within central hub 54, are formed from a rigid material such as stainless steel.

Figure 8:
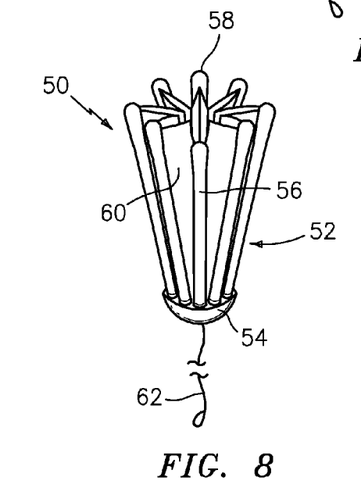
FIG. 8 is a side view of the vaginal pessary of FIG. 6 showing the frame member in a collapsed state.

Flexible and resilient sheet-like material 60, which connects (and preferably also coats) the spokes 56 of frame member 52, is a thin, membrane-like, biocompatible material that folds inward upon collapse of frame member 52 (see FIG. 8). In a preferred embodiment, material 60 is formed from a material selected from the group of polyethylene, polyvinyl chloride, urethane, silicone rubber, and the like.

Withdrawal means 62, which is attached to central hub 54 of frame member 52 may be any device for physically withdrawing pessary 50 from the vagina. These devices, which are mentioned above in relation to the first embodiment as including cords, strings and tapes, may be made of any suitable material known in the prior art including, but are not limited to, cotton, cellulose, rayon, polyolefin (e.g., polyethylene, polypropylene), nylon, silk and polyester. In a preferred embodiment, withdrawal means 52 is a cord or string made from cotton, rayon or polypropylene that has a length ranging from about 10 to about 20 cm.

Insertion and removal of vaginal pessary 50 may be easily and comfortably performed by a patient on a daily basis, or as needed, using insertion/withdrawal device 64 (see FIG. 9). Insertion/withdrawal device 64 comprises: an elongate cylindrical body 66 having an inner diameter that is slightly larger than the maximum outer diameter of collapsed pessary 50, and having a slot-shaped opening 68 located along its longitudinal axis; and a plunger 70. To insert pessary 50 into the vagina, the patient would remove plunger 70 from device 64, draw the pessary 50 into the device 64 using withdrawal means 62, and then the patient would replace plunger 70. Device 64 would then be inserted into the vagina and upon proper placement therein, the patient would push on plunger 70 to eject vaginal pessary 50 from device 64, whereupon it would immediately assume its normal open, substantially conical configuration in the vagina (see FIG. 10), with proximal ends 58 of spokes 56 contacting the inner wall of the vagina. Device 64 would then be removed by the patient from the vagina, cleaned and stored.

When the patient is ready to remove the vaginal pessary 50, she would grasp withdrawal means 62 with one hand and re-insert device 64 (without plunger 70) into the vagina with the other hand, while guiding withdrawal means 62 through slot-shaped opening 68 of device 64. Once device 64 contacted pessary 50 within the vagina, the patient would slowly urge pessary 50 into device 64 by applying a downward force on withdrawal means 62. Once pessary 50 had been completely drawn inside device 64, device 64 would be removed from the vagina, the pessary 50 and device 64 cleaned and the pessary 50 stored within device 64 until it was needed again by the patient.

Figure 10:
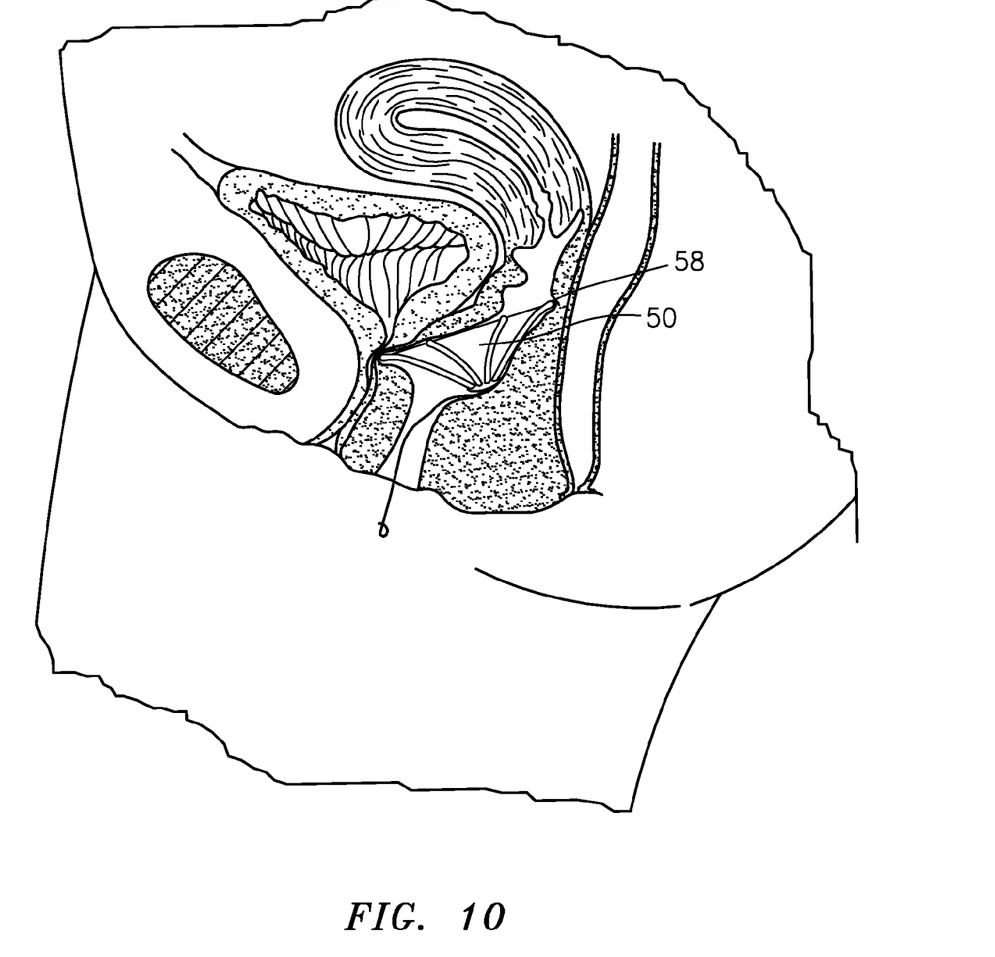
FIG. 10 is a diagrammatic cross-sectional view of the female urogenital system showing the vaginal pessary of FIG. 6 in place within the vagina.
Figure 11:
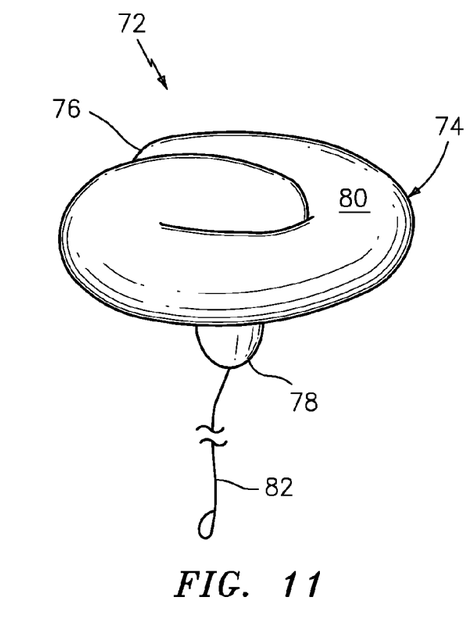
FIG. 11 is a top perspective view of a variation of the third embodiment of the vaginal pessary of the present invention showing the pessary in its normally flat or planar, coiled configuration.

As best shown in FIG. 10, which is a diagrammatic cross-sectional view of the female urogenital system showing open vaginal pessary 50 (as shown in FIG. 6) in place within the vagina, vaginal pessary 50 fully and effectively counters the effects of any prolapsing organ, such as the urinary bladder, uterus or rectum, into the vagina or vaginal vault.

Referring now to FIGS. 11 to 16, in detail, reference number 72 has been used to generally designate three variations of a third embodiment of the vaginal pessary of the present invention. In this third embodiment, vaginal pessary 72 is a yieldably extensible, self-retracting vaginal pessary that basically comprises:

(a) an elongate cylindrical body 74 having a distal end 76 and a proximal end 78, the elongate cylindrical body 74 normally assuming a coiled configuration;
(b) optionally, a protective cover or sleeve 80 for encasing the elongate cylindrical body 74; and
(c) withdrawal means 82 attached to the proximal end 78 of the elongate cylindrical body 74.

Figure 14:
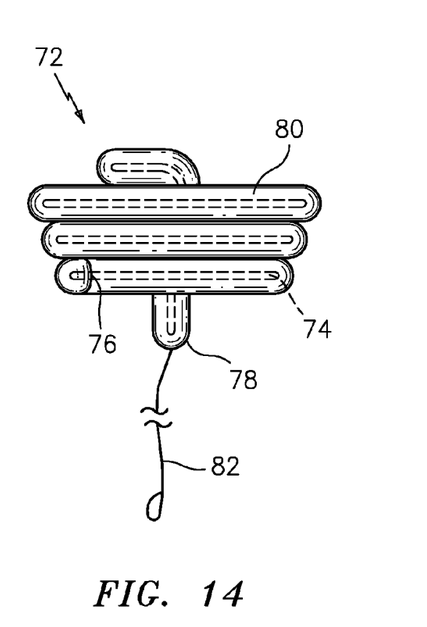

By way of example, and as best shown in FIGS. 11 to 14, elongate cylindrical body 74 may normally assume a planar or flat, coiled configuration (FIGS. 11 and 12), a non-planar, substantially diamond-shaped, coiled configuration (FIG. 13), or a non-planar, substantially cone-shaped, coiled configuration (FIG. 14).

Vaginal pessary 72, when in its normally coiled state, has a maximum outer diameter that exceeds the midsagittal vaginal diameter and is sufficiently stiff to resist deforming stresses exerted by the vaginal wall muscles while in place in the vagina.

Figure 15:
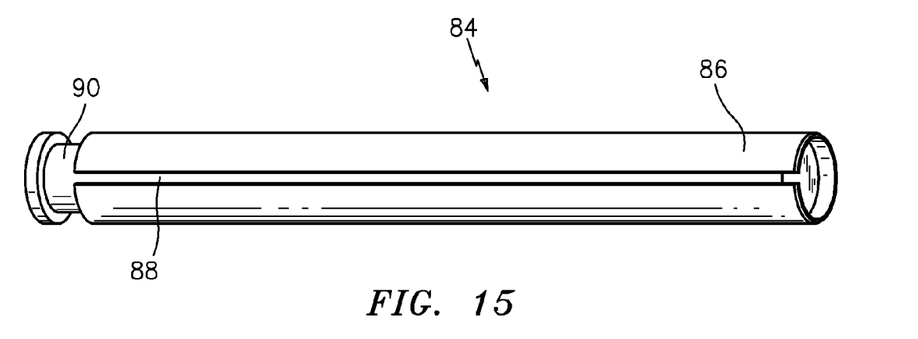
FIG. 15 is a side view of a device for inserting and removing the vaginal pessary of FIGS. 11, 13 and 14 into and out of the vagina.

The elongate cylindrical body 74 of vaginal pessary 72, when forcibly extended or stretched out, fits inside any appropriate insertion/withdrawal tool or device, such as that shown in FIG. 15. Preferably, the elongate cylindrical body 74, when forcibly elongated, has a maximum outer diameter that does not exceed 2.5 cm.

Vaginal pessary 72, in its normally coiled state, is sized or dimensioned to suit the individual requirements of the patient. It is intended that the vaginal pessary of this third embodiment be available in a number of sizes, with maximum outer pessary diameters ranging from about 5.0 to about 9.0 cm, and pessary heights ranging from about 2.5 to about 4.5 cm.

As noted above, the elongate cylindrical body 74 assumes a coiled configuration when relaxed, and requires the application of an external force in order to assume a different configuration, such as being elongated. Conversely, when elongate cylindrical body 74 is elongated or otherwise manipulated by a force so that it is no longer in a related configuration, it continuously exerts an opposing force until it reassumes the relaxed configuration.

Elongate cylindrical body 74 may be prepared from any "elastic memory" or "elastic shape memory" material. The terms "elastic memory" and "elastic shape memory" are used herein to mean a material that has spring-like properties, that is, a material capable of being deformed by an applied stress and springing back to its original unstressed shape or configuration when that stress is removed.

In one preferred embodiment, elongate cylindrical body 74 is formed from a flexible, thermoplastic material that is thermoformed into a coiled shape and is biased to retain that shape, or retract into it, because of its elastic memory. In a more preferred embodiment, elongate cylindrical body 74 is formed from polyvinyl chloride.

In another preferred embodiment, elongate cylindrical body 74 is formed from a helical spring, or from an elongated spring metal ribbon or blade, that normally adopts a coiled configuration as described above.

Figure 12:
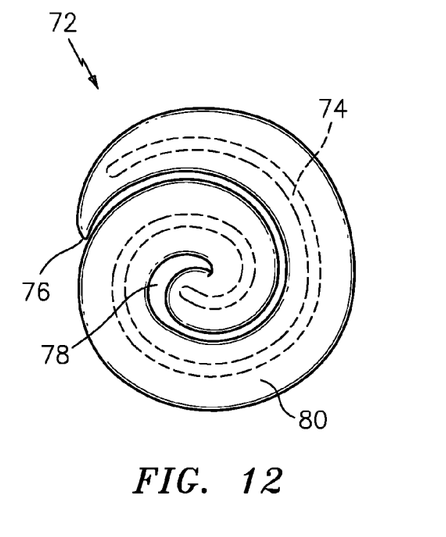
FIG. 12 is a top plan view of the pessary shown in FIG. 11.
Figure 13:
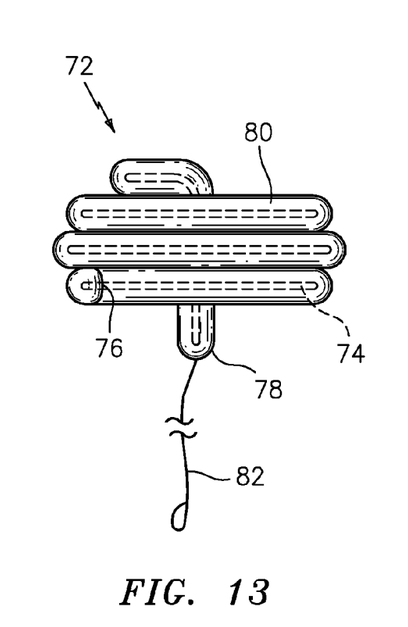
FIGS. 13 and 14 are side perspective views of other variations of the third embodiment of the inventive vaginal pessary showing each pessary in its normally non-planar, coiled configuration.

Elongate cylindrical body 74 may have blunt, rounded or shaped distal and proximal ends 76, 78. In a preferred embodiment, as best shown in FIG. 12, elongate cylindrical body 74 normally assumes a flat, coiled configuration, and distal end 76 of elongate cylindrical body 74 is shaped to conform to the substantially circular outer circumference of the vaginal pessary.

In another preferred embodiment, contiguous side edges of body 74 may be adapted to mate or interconnect as the body 74 returns to its relaxed position.

A protective cover or sleeve 80 may be used to encase the elongate cylindrical body 72. Protective cover or sleeve 80 may be made of a flexible and impermeable biocompatible material. Suitable materials include polyethylene, polyvinyl chloride, urethane, silicone rubber, and the like.

Withdrawal means 82, which is attached to the proximal end 78 of the elongate cylindrical body 74, may be any device for physically withdrawing pessary 72, from the vagina. In a preferred embodiment, withdrawal means 82 is a cord or string having a length ranging from about 18 to about 35 cm that is made from cotton, rayon or polypropylene.

In a more preferred third embodiment, as best shown in FIG. 12, vaginal pessary 72 comprises:
(a) an elongate cylindrical body 74 formed from a flexible, thermoplastic material that has been thermoformed into a flat, coiled shape, wherein the elongate cylindrical body 74 is biased to retain such a flat, coiled shape;
(b) a silicone protective cover or sleeve 80 that fully encases the elongate cylindrical body 74; and
(c) a cord or string (not shown in FIG. 12) made from cotton, rayon or polypropylene that is attached to the proximal end of the elongate cylindrical body.

Insertion and removal of vaginal pessary 72 may be easily and comfortably performed by a patient on a daily basis, or as needed, using insertion/withdrawal device 84 (see FIG. 15). Insertion/withdrawal device 84 comprises: an elongate cylindrical body 86 having an inner diameter that is slightly larger than the outer diameter of the elongate cylindrical body 74, of vaginal pessary 72, and having a slot-shaped opening 88 located along its longitudinal axis; and a plunger 90. To insert pessary 72, into the vagina, the patient would remove plunger 90 from device 84, draw the pessary 72, into the device 84 using withdrawal means 82, and then the patient would replace plunger 90. Device 84 would then be inserted into the vagina and upon proper placement therein, the patient would push on plunger 90 to eject vaginal pessary 72, from device 84, whereupon it would immediately assume its normal coiled configuration in the vagina (see FIG. 16). Device 84 would then be removed by the patient from the vagina, cleaned and stored.

When the patient is ready to remove the vaginal pessary 72, she would grasp withdrawal means 82 with one hand and re-insert device 84 (without plunger 90) into the vagina with the other hand, while guiding withdrawal means 82 through the slot-shaped opening 88 of device 84. Once device 84 was in place within the vagina, the patient would slowly urge pessary 72, into device 84 by applying a downward force on withdrawal means 82. Once pessary 72, has been completely drawn into device 84, device 84 would be removed from the vagina, the pessary 72, and device 84 cleaned and the pessary 72, stored within device 84 until it was needed again by the patient.

Figure 16:
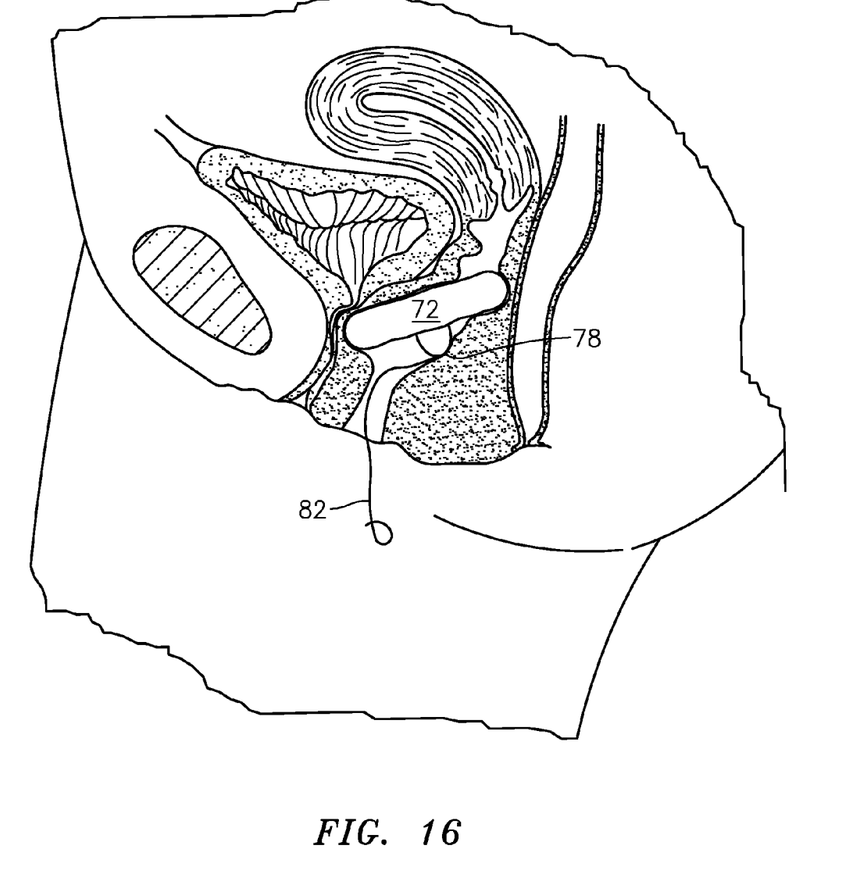
FIG. 16 is a diagrammatic cross-sectional view of the female urogenital system showing the vaginal pessary of FIG. 11 in place within the vagina.

As best shown in FIG. 16, which is a diagrammatic cross-sectional view of the female urogenital system showing coiled vaginal pessary 72 in place within the vagina, vaginal pessary 72 fully and effectively counters the effects of any prolapsing organ, such as the urinary bladder, uterus or rectum, into the vagina or vaginal vault.

While various embodiments of the present invention have been described above, it should be understood that they have been presented by way of example only, and not limitation. Thus, the breadth and scope of the present invention should not be limited by any of the exemplary embodiments.

Having thus described the invention, what is claimed is:

1. A vaginal pessary for managing pelvic organ prolapse, which comprises: (a) an open, substantially cone-shaped, collapsible frame member, the frame member being biased to an open position and comprising an inverted substantially dome-shaped central hub for pressing against a vaginal wall and anchoring the pessary within a vaginal cavity, and a plurality of flexible and resilient spokes emanating from the dome-shaped central hub; (b) a flexible and resilient sheet-like material connecting the spokes of the frame member; and (c) withdrawal means attached to the central hub of the frame member.

2. The vaginal pessary of claim 1, wherein each spoke emanating from the central hub of the frame member has a proximal end, and wherein the frame member has a transverse cross-sectional shape formed by the proximal ends of the spokes of the frame member, the transverse cross-sectional shape being selected from the group of circular, oval, semi-oval, elliptical, and semi-elliptical cross-sectional shapes.

3. The vaginal pessary of claim 2, wherein the transverse cross-sectional shape of the frame member is circular.

4. The vaginal pessary of claim 2, wherein the transverse cross-sectional shape of the frame member is elliptical.

5. The vaginal pessary of claim 1, which when in its collapsed state has a maximum outer diameter or width ranging from about 2.5 to about 4.5 centimeters.

6. The vaginal pessary of claim 1, which when in its normally open state has a maximum outer diameter or width ranging from about 5.0 to about 9.0 centimeters.

7. The vaginal pessary of claim 1, wherein the central hub of the frame member and the sheet-like material connecting the spokes of the frame member are formed from a material selected from the group of polyethylene, polyvinyl chloride, urethane and silicone rubber, and wherein the spokes are formed from stainless steel.

8. The vaginal pessary of claim 1, wherein the withdrawal means comprises a cord or string having a length ranging from about 10 to about 20 centimeters.

9. The vaginal pessary of claim 1, which when in its normally open state has a maximum height ranging from about 2.5 to about 4.5 centimeters.

10. A device for use with a vaginal pessary for managing pelvic organ prolapse that comprises: (a) an open, substantially cone-shaped, collapsible frame member, the frame member being biased to an open position and comprising an inverted substantially dome-shaped central hub for pressing against a vaginal wall and anchoring the pessary within a vaginal cavity, and a plurality of flexible and resilient spokes emanating from the dome-shaped central hub; (b) a flexible and resilient sheet-like material connecting the spokes of the frame member; and (c) withdrawal means attached to the central hub of the frame member, wherein the device comprises an elongate cylindrical body having a slot-shaped opening located along its longitudinal axis, and a plunger slidably arranged within a portion of the elongate cylindrical body.

11. A method of using a device comprising: (a) an open, substantially cone-shaped, collapsible frame member, the frame member being biased to an open position and comprising a central hub and a plurality of flexible and resilient spokes emanating from the central hub; (b) a flexible and resilient sheet-like material connecting the spokes of the frame member; and (c) withdrawal means attached to the central hub of the frame member, which method comprises positioning the device within a vaginal cavity to support prolapsed pelvic organs, the central hub pressing against a vaginal wall and anchoring the device within the vaginal cavity.

* * * * *